United States Patent [19]

Lynch et al.

[11] Patent Number: 4,828,849

[45] Date of Patent: May 9, 1989

[54] SURFACTANT INHIBITION OF DENTAL PLAQUE

[75] Inventors: Donald M. Lynch, Flemington; Benjamin Appelbaum, Flanders, both of N.J.

[73] Assignee: Warner-Lambert Company, Morris Plains, N.J.

[21] Appl. No.: 143,986

[22] Filed: Jan. 14, 1988

[51] Int. Cl.$^4$ .......................... A61K 7/16; A61K 7/18
[52] U.S. Cl. .......................................... 424/52; 424/49
[58] Field of Search ............................... 424/49, 52, 54

[56] References Cited

U.S. PATENT DOCUMENTS

| | | | |
|---|---|---|---|
| 3,897,548 | 7/1975 | Katz | 424/54 |
| 3,937,807 | 2/1976 | Haefele | 424/54 |
| 4,022,880 | 5/1977 | Vinson | 424/54 |
| 4,051,234 | 9/1977 | Gieske | 424/54 |
| 4,067,962 | 1/1978 | Juneja | 424/54 |
| 4,117,109 | 9/1978 | Stookey | 424/52 |
| 4,122,163 | 10/1978 | Muhler | 424/52 |
| 4,205,061 | 5/1986 | Vidra | 424/55 |
| 4,416,867 | 11/1983 | Ritchey | 424/49 |
| 4,425,325 | 1/1984 | Ritchey | 424/54 |
| 4,428,928 | 1/1984 | Muhler | 424/49 |
| 4,627,452 | 3/1987 | Ritchey | 424/54 |

*Primary Examiner*—Shep K. Rose
*Attorney, Agent, or Firm*—Gary M. Nath

[57] ABSTRACT

The invention provides an oral preparation or composition such as a mouthwash, mouthrinse, toothpaste and the like containing certain classes of surfactants which act to inhibit plaque formation by inhibiting the initial adherence of bacteria to the dentin surfaces and in the case of one class of surfactants additionally inhibiting the glucosyl transferase catalysis to prevent the synthesis of extracellular polysaccharides from sucrose.

The surfactants comprise substituted taurines, substituted isethionates and substituted hydroxy sultaines in which the substituents are long chain hydrocarbon radicals. The surfactants are employed in the aqueous-based oral compositions at concentrations between about 0.00001M to 0.1M to effect inhibition.

25 Claims, No Drawings

SURFACTANT INHIBITION OF DENTAL PLAQUE

BACKGROUND OF THE INVENTION

This invention is concerned with a method of inhibiting the formation of dental plaque which employs certain surfactants and oral compositions containing such surfactants.

Dental plaque is a dense, heterogeneous, non-calcified bacterial mass which firmly adheres to the tooth surface to the degree that it resists wash off by salivary flow. The bacteria contained in plaque possess varying degrees of pathogenic activity and are responsible in part for dental caries, gingivitis, mouth odor and periodontal disease. *Streptococcus mutans* is one of the bacteria found in dental plaque and it has been found to possess a high cariogenic potential in a variety of laboratory animals. *Actinomyces viscosus*, another dental plaque bacteria, has been associated with gingivitis and root surface caries. Obviously the removal or inhibition of plaque formation would significantly reduce the occurences of these diseases.

Plaque is generally removed by employing mechanical cleaning using an abrasive dentifrice, by flossing or by rinsing with an antibacterial (anti-plaque) mouthrinse. However, plaque deposited between teeth is difficult to remove by mechanical cleaning and flossing does not remove plaque located at the gingival margin. Anti-plaque mouthrinses serve as an adjunct to mechanical plaque removal. To date, an anti-plaque mouthrinse that can take the place of mechanical plaque removal has not been discovered. Mouthrinses are often ineffective at the later stages of plaque development and are useless if the plaque has become calcified to form calculus or tartar.

Plaque formation on a clean tooth, it is generally believed, starts with the formation of a pellicle or cuticle composed of salivary constituents. The pellicle is an amorphous, membranous layer which covers the enamel surface and is considered to consist of salivary glycoproteins, polypeptides and other salivary constituents which have become selectively adsorbed on the tooth surface. The pellicle is usually free of bacteria. The pellicle is formed within minutes after the tooth is cleaned and the adsorbed materials eventually become transformed into a highly insoluble coating. Thereafter an initial adherence of bacterial occurs on the acquired pellicle. Thereafter bacteria produce extracellular polysaccharides (called glucans) from sucrose catalyzed by the enzyme glucosyl transferase which aid entrapment and adherence of other bacteria.

The cariogenic potential of *S. mutans* for example, is associated with its ability to form dental plaque and this ability is dependent upon the synthesis of extracellular polysaccharides from sucrose.

In addition to initial adherence and glucosyltransferase catalysis which aids adherence the coaggregation of varous species of bacteria occurs in which specific bacteria attach to each other by synthesizing polymers which bind similar and dissimilar cells together although there are some species that will not coaggregate.

In an effort to rid teeth of plaque the prior art has described agents incorporated into oral preparations such as dentifrices which inhibit the formation of plaque rather than its removal as described above.

In U.S. Pat. No. 4,117,107 for example, a method for retarding pellicle and plaque formation is described which includes contacting sites of plaque formation and growth with a dental preparation containing certain fatty acid amido betaines.

Similarly, U.S. Pat. No. 4,130,637 provides betaine compounds derived from higher alkyl dimethyl carboxylic acid quarternary ammonium compounds effective in controlling dental plaque without producing an esthetically unacceptable discoloration of the teeth.

U.S. Pat. No. 4,360,515 provides compounds for the prevention of attachment of dental plaque to the teeth comprising certain sulfonated alkoxynaphthalenes and the pharmaceutically acceptable salts thereof.

U.S. Pat. No. 4,619,825 describes a plaqueinhibiting composition comprising an aqueous dispersion of emulsan which can be incorporated in dental preparation toothpastes or mouthwashes.

U.S. Pat. No. 3,981,989 deals with an oral preparation for the prevention of tooth decay containing dextranase stabilized with a special protein such as gelatin or peptone. Nonionic surfactants may also be added with an anionic surfactant to impart stability to the dextranase. Sodium acyltaurate is a suitable anionic surfactant and is preferably present to the extent of 0.5% to 5% by weight of the oral preparation.

British Patent Specification No. 990,957 describes a strontium ion-containing toothpaste for treatment of hypersensitive dentin which contains, inter alia, compatible surface-active foaming agents including fatty-acid N-methyl taurine condensates.

The present invention, on the other hand, provides an effective plaque inhibiting composition containing certain classes of surfactants which act to prevent the initial adherence of bacteria and the formation of extracellular polysaccharides from bacteria which are catalysed by glucosyl transferase in the formation of plaque and therefor substantially inhibit its formation. The surfactants are effective in very low concentrations and are suitable for use in oral compositions.

SUMMARY OF THE INVENTION

In brief, the invention provides an oral preparation or composition such as a mouthwash, mouthrinse, toothpaste and the like containing certain classes of surfactants which act to inhibit plaque formation by inhibiting the initial adherence of bacteria to the dentin surfaces and in the case of one class of surfactants additionally inhibiting the glucosyl transferase catalysis to prevent the synthesis of extracellular polysaccharides from sucrose.

The surfactants comprise substituted taurines, substituted isethionates and substituted hydroxy sultaines in which the substituents are long chain hydrocarbon radicals. These surfactants are employed in aqueous-based oral compositions at concentrations between about 0.00001M to 0.1M to effect inhibition. Concentrations of the surfactants to effect 50% inhibition of plaque formation are significantly less than the concentrations of the surfactants in other products.

DETAILED DESCRIPTION OF THE PREFERRED EMBODIMENTS

The plaque inhibitory agents of the present invention comprise three classes of surfactants.

The first class of surfactants are substituted taurines represented by formula (1) below:

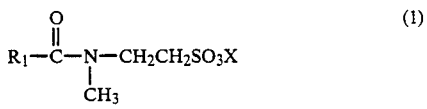

Wherein $R_1$ is an organic hydrocarbon radical containing from aout 10 to 24 carbon atoms, preferably from 12 to 20 carbon atoms and X is hydrogen, an alkali metal or ammonium salt. X is preferably sodium or potassium. Exemplary of such surfactants are the sodium salts of N-methyl-N-cocoyltaurine, N-methyl-N-oleoyltaurine and N-methyl-N-palmitoyltaurine.

The second class of surfactants are substituted isethionates represented by formula (2) below:

wherein $R_1$ and X are as described above. A typical and useful isethionate surfactant is cocoyl sodiumisethionate.

The third class of surfactants are substituted hydroxy sultaines represented by formula (3) below:

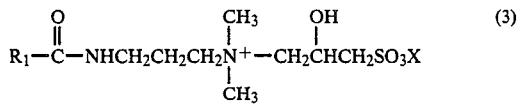

wherein $R_1$ and X are as described above. Exemplary of such hydroxy sultaines are cocamidopropylhydroxy sultaine, sodium salt.

The substituted taurines of the invention are effective both in inhibiting the initial adherence of bacteria to tooth surfaces and the glucosyl transferase catalysis. The isethionates and hydroxy sultaines are inhibitors of initial adherence. When incorporated into aqueous-based oral compositions the effective concentrations of the surfactants can vary between 0.00001M to 0.1M based on the aqueous media. In the case of the substituted taurine surfactants of the invention concentrations of between about 0.00008M to 0.005M will effect 50% inhibition of the adherence of bacteria using as an in vitro model the adherence to saliva-coated hydroxy apatite beads, which simulate actual dental enamel. Concentrations between 0.0002M and 0.0004M are particularly preferred. Such taurines also inhibit 50% of glucosyl transferase activity at concentrations of about 0.001M. The isethionate surfactants effect 50% inhibition of bacterial adherence at concentrations of about 0.0001M and the hydroxy sultaine surfactants effect 50% inhibition at concentrations between 0.001M and 0.03M.

The low concentrations of these surfactants found to effect 50% inhibition of plaque formation are significantly less than the concentrations of these agents routinely used in other products. The surfactants can thus exert their anti-plaque effect at concentrations much less than that needed to exert their other chemical effects in formulations.

The anti-plaque surfactants of the invention can be readily incorporated into aqueous or aqueous/alcohol-containing oral compositions such as a mouthwash, spray, rinse, toothpaste, dental cream, gel or toothpowder.

The surfactants should be present in amounts of from about 0.002% to about 2.0% by weight of the total weight of the composition. Preferably the surfactant is present in amounts from about 0.02% to about 1% by weight of the total weight and most preferably from about 0.05% to about 0.5%.

In one form of the invention, the oral composition may be a liquid such as a mouthwash, spray or rinse. In such a composition the vehicle is typically a water/alcohol mixture. Generally the ratio of total water to alcohol is in the range of from about 1:1 to about 20:1, preferably about 3:1 to about 20:1 and most preferably about 3:1 to about 10:1 by weight. The total amount of water/alcohol mixture in a mouthwash preparation is typically in the range from about 45% to about 82.5% by weight of the composition. The pH value of such mouthwash preparation is generally from about 4 to about 9 and preferably from about 5 to about 7. A pH below 4 is irritating to the oral cavity and a pH greater than 9 results in an unpleasant mouth feel.

Fluorine providing compounds may be present in the oral preparations of this invention. These compounds may be slightly water-soluble or may be fully water-soluble and are characterized by their ability to release fluoride ions or fluoride-containing ions in water. Typical fluorine providing compounds are inorganic fluoride salts such as soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and difluorophosphate and fluorinated sodium calcium pyrophosphate.

Alkali metal, tin fluoride and monofluorophosphates such as sodium and stannous fluoride, sodium monofluorophosphate and mixtures thereof are preferred.

In an oral liquid composition such as a mouthwash, the fluorine providing compound is generally present in an amount sufficient to release up to about 0.15%, preferably about 0.001% to about 0.1% and most preferably from about 0.001% to about 0.05% fluoride by weight of the preparation.

The oral composition may also contain additional flavorants and colorants.

In the instance where auxiliary sweeteners are utilized, the present invention contemplates the inclusion of those sweeteners well known in the art, including both natural and artificial sweeteners. Thus, additional sweeteners may be chosen in minor amounts from the following non-limiting list.

A. Water-soluble sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol xylitol, mannitol and mixtures thereof.

B. Water-soluble artificial sweeteners such as the soluble cyclamate salts and the like.

C. Dipeptide based sweeteners such as L-phenylalanine methyl ester and materials described in U.S. Pat. No. 3,492,131 and the like.

In general, the amount of sweetener will vary with the desired amount of sweeteners selected for a particular oral preparation. This amount will normally be 0.01% to about 40% by weight. The water-soluble sweeteners described in category A above, are preferably used in amounts of about 5% to about 40% by weight, and most preferably from about 10% to about 20% by weight of the final composition. In contrast, the artificial sweeteners described in categories B and C are used in amounts of about 0.005% to about 5.0% and most preferably about 0.05% to about 2.5% by weight of the final composition. These amounts are ordinarily necessary to achieve a desired level of sweetness independent from the flavor level achieved from flavorants.

Suitable flavorings include both natural and artificial flavors, and mints such as peppermint and spearmint. Citrus flavors such as orange and lemon, various fruit flavors, both individual and mixed, and the like are contemplated. The flavorings are generally utilized in amounts that will vary depending upon the individual flavor, and may, for example, range in amounts of about 0.05% to about 6% by weight of the final composition.

The colorants useful in oral compositions of the present invention include pigments which may be incorporated in amounts of up to about 2% by weight of the composition. Also, the colorants may include other dyes suitable for food, drug and cosmetic applications, known as FD & C and D & C dyes. The materials acceptable for the foregoing spectrum of use are preferably watersoluble. Illustrative examples include the yellow dye, known as D & C Yellow #10, and the dye known as FD & C Green #3 which comprises a triphenylmethane dye. A full recitation of all FD & C and D & C colorants useful in the present invention and their corresponding chemical structures may be found in the Kirk-Othmer Encyclopedia of Chemical Technology, 3rd Edition, in Volume 6, at pages 561–595, which text is accordingly incorporated herein by reference.

The oral compositions may also be substantially solid or pasty in character such as a dental cream, toothpaste or a toothpowder. Solid or pasty oral preparations contain polishing materials. Typical polishing materials are abrasive particulate materials having particle sizes of up to about 20 microns. Nonlimiting illustrative examples include: water-insoluble sodium metaphosphate, potassium metaphosphate, tricalcium phosphate, dihydrated calcium phosphate, calcium pyrophosphate, magnesium orthophosphate, trimagnesium phosphate, calcium carbonate, alumina, aluminum silicate, zirconium silicates, silica, bentonite, and mixtures thereof. Polishing materials are generally present in an amount from about 20% to about 82% by weight of the oral preparation. Preferably, they are present in amounts from about 20% to about 75% in toothpaste, and from about 70% to about 82% in toothpowder. For toothpaste and dental creams the water content is about 25% to 50% by weight.

In clear gels, a polishing agent of colloidal silica and alkali metal aluminosilicate complexes are preferred since they have refractive indicies close to the refractive indicies of gellin agent liquid systems commonly used in dentifrices.

In general, the anti-plaque oral compositions of the present invention are prepared as follows. The sweetener is dissolved in water to form a solution. The anti-plaque surfactant is added to the solution and mixed until dissolved. Then sufficient water alcohol or mixtures thereof are added with mixing until the final solution volume is reached. When colorants, additional sweeteners and similar additives are included in the composition, they are added at the same time the sweetener is added. The anti-plaque surfactant may also be added as the final ingredient.

In order to more fully describe the present invention, the following non-limiting Examples are submitted.

EXAMPLE 1

This Example demonstrates the inhibition of initial adherence of bacteria to tooth surfaces by the surfactants of the invention using an in vitro model, adherence to saliva-coated hydroxyapatite.

Adherence Assay

Three strains of bacteria were used in this Example, Streptococcus sanguis G9B, S. mutans Ingbritt and Actinomyces viscosus $T_{14}V$. Among the oral bacteria, Streptococcus sanguis interacts with salivary glycoproteins involved with pellicle formation and has been shown to be one of the first organisms to colonize a tooth surface. S. sanguis G9B adheres well to saliva-coated hydroxyapatite. This attachment, in vivo, occurs within minutes. As plaque matures, the percentage of S. sanguis decreases, but its actual numbers remain high. In vivo and in vitro studies have shown S. sanguis to interact with other oral bacteria including S. mutans and Actinomyces viscosus. S. mutans has also been implicated as a cause of dental caries. Stock cultures were kept both lyophilized and frozen in Brain Heart Infusion Broth (BHI, Difco Laboratories) at $-70°$ C.; the latter being used to inoculate starter cultures. After overnight incubation at 37° C, a 0.5% inoculum was used to inoculate 100 ml of BHI which was subsequently incubated 20 hours at 37° C. The cells were radioactively labeled by adding tritiated thymidine (methyl-3H) to a final specific activity of 2 $\mu$Ci/ml. After incubation, the cells were harvested by centrifugation (16,320× g, 15 minutes, 4° C.), washed three times with buffered KCl (2 mM potassium phosphate buffer, 1 mM $CaCl_2$, and 5 mM KCl, pH 6.0) (Ref. 8), and resuspended to a turbidity of 300 Klett units (Klett-Summerson colorimeter; blue, #47 filter). This bacterial stock cell suspension was then diluted with buffered KCl to produce a series of cell suspensions ranging from 1.6 to 300 Klett units. Duplicate 50 ul aliquots of each cell suspension were counted in Aquasol-2 to determine their specific activities.

A. viscosus $T_{14}V$ was grown for 48 hours at 37° C. under anaerobic conditions in tryptic soy broth (TSB) containing glucose.

Preparation of Saliva

Whole, paraffin-stimulated saliva was collected into ice-chilled tubes and clarified by centrifugation (16,3200× g, 15 minutes, 4° C.). The supernatant fluids were removed and aliquots were stored frozen at $-20°$ C. until used. A pool of saliva from several individuals was used routinely; and was collected after a 10 hour fast with no food or oral hygiene on the morning of collection.

Adherence Assay

Spheroidal hydroxyapatite beads (manufactured by BDH Chemicals, Poole, England and obtained from Gallard-Schlessinger Co., Carle Place, NY) were distributed into a 12×75 mm polystyrene test tube (Walter Sarstedt, Inc., Princeton, N.J.) and mixed with either 1 ml of saliva or buffered KCl for 1.5 hours at ambient temperature with rotation (20 rpm). Each tube contained 40±2 mg of HA beads, distributed using a calibrated stainless steel ladle.

The cells were radioactively labelled by addition of 1.5 $\mu$Ci/ml methyl-$^3$H thymidine to the cell suspension media. The hydroxyapatite (HA) beads were coated with either a surfactant or a control or saliva and rotated for 30 minutes at ambient temperature. The excess agent or saliva was removed by washing with buffer. Radioactively-labelled cells suspended in either buffer or varying concentrations of the surfactant were added to the beads. The beads and cells were incubated at 37° C., 10 minutes for the streptococcal strains and 15 minutes for the actinomycete, after which the beads were washed to remove the unbound cells and the radioactivity bound to them was determined by scintillation counting. *S. mutans* Ingbritt was also assayed for sucrose-mediated adherence by addition of 1% sucrose to the cells and surfactant mixture. The concentration to effect 50% inhibition of bacterial adherence to the HA beads was determined graphically.

Several surfactant agents according to the invention dissolved in water were employed in the assay.

The results are summarized in Table 1 below.

TABLE 1

| Surfactant | 50% Inhibition Concentration (M) |
|---|---|
| 1. N—methyl-N—palmitoyltaurine, sodium salt (IGEPON TN-74; GAF Corp.) | $2.5 \times 10^{-4}$ |
| 2. N—methyl-N—oleoyltaurine sodium salt (IGEPON T-33; GAF Corp.) | $3.5 \times 10^{-4}$ |
| 3. N—methyl-N—cocoyltaurine sodium salt (IGEPON TC-42; GAF Corp.) | $3.0 \times 10^{-4}$ |
| 4. Cocamidopropylhydroxysultaine (Schercotaine SCAB; Scher Co.) | $1.5 \times 10^{-2}$ |
| 5. Cocamidopropylhydroxysultaine, potassium salt (Schercotaine SCAB-KG; Scher Co.) | $2.5 \times 10^{-2}$ |
| 6. Cocoylisethionate, sodium salt Tauranol I-78 | $1.0 \times 10^{-4}$ |

As table 1 shows, concentrations ranging from 0.0001M to 0.001M were sufficient to effect a 50% inhibition of initial adherence of bacteria to saliva-coated hydroxyapatite.

EXAMPLE 2

This Example demonstrates the inhibition of glucosyl transferase catalysis by the surfactants of the invention.

An assay for the inhibition of glucosyl transferase activity was developed wherein the enzyme was incubated for 10 minutes with varying concentrations of the surfactant in 0.05M sodium acetate buffer, pH 5.5 at 37° C., with agitation. The reaction was then started by adding the remainder of the assay mixture (to a final volume of 450 mcl) consisting of: 2.5 μCi uniformly-labelled $14_C$-sucrose, 1% unlabelled sucrose, sodium fluoride and Dextran $T_{10}$ in acetate buffer. Samples were removed at timed intervals, spotted to filters and the filters were treated with methanol. Radioactivity incorporated into glucan was plotted versus time as compared to a control preparation. By this procedure the concentration of test reagent necessary to achieve 50% inhibition of glucosyl transferase activity was determined. The results are summarized in Table 2 below.

TABLE 2

| Surfactant | 50% Inhibition Concentration (M) |
|---|---|
| 1. N—methyl-N—palmitoyltaurine, sodium salt | $1 \times 10^{-3}$ |
| 2. N—methyl-N—oleoyltaurine sodium salt | $1 \times 10^{-3}$ |
| 3. N—methyl-N—cocoyltaurine | $1 \times 10^{-3}$ |

TABLE 2-continued

| Surfactant | 50% Inhibition Concentration (M) |
|---|---|
| sodium salt | |

As Table 2 shows, a taurine surfactant concentration of 0.001M was sufficient to inhibit 50% of the glucosyl transferase activity.

I claim:

1. An oral composition in aqueous media consisting essentially of from 0.00001M to 0.1M of a surfactant effective to inhibit dental plaque selected from the group consisting of

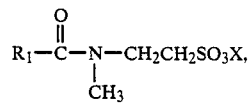

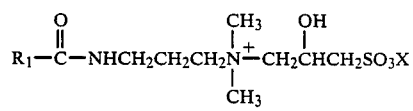

wherein $R_1$ is an organic hydrocarbon radical containing from about 10 to 24 carbon atoms, and X is selected from the group consisting of hydrogen, an alkali metal and ammonium and wherein the surfactant further comprises an effective plaque-inhibiting concentration of from 0.002 to less than 0.5 weight percent of the composition.

2. The oral composition of claim 1 wherein $R_1$ is an organic hydrocarbon radical containing from 12 to 20 carbon atoms.

3. The oral composition of claim 1 wherein X is sodium.

4. The oral composition of claim 1 wherein

is cocoyl.

5. The oral composition of claim 1 wherein

is oleoyl.

6. The oral composition of claim 1 wherein

is palmitoyl.

7. The oral composition of claim 1 which comprises a mouthwash.

8. The oral composition of claim 1 which comprises a toothpaste.

9. The oral composition of claim 1 which comprises a mouthrinse.

10. The oral composition of claim 1 which comprises a dental cream.

11. The oral composition of claim 1 which comprises a toothpowder.

12. The oral composition of claim 1 wherein said aqueous media is an alcohol/water mixture.

13. The oral composition of claim 12 which wherein the ratio of water to alcohol is from about 1:1 to about 20:1.

14. The oral composition of claim 1 which further comprises a fluorine-providing compound.

15. The oral composition of claim 1 which further comprises a flavorant.

16. The oral composition of claim 1 which further comprises a colorant.

17. The oral composition of claim 1 which further comprises a natural or artificial sweetener.

18. The oral composition of claim 1 wherein said surfactant is represented by the formula

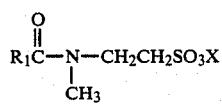

and is present in said oral composition at concentrations between about 0.00008M to 0.005M.

19. The oral composition of claim 1 wherein said surfactant is represented by the formula

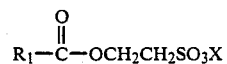

and is present in said oral composition at concentrations of about 0.0001M.

20. The oral composition of claim 1 wherein said surfactant is represented by the formula

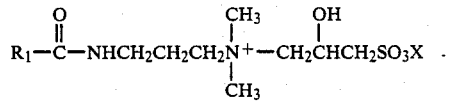

and is present in said oral composition at concentrations between about 0.001M and 0.03M.

21. A method for inhibiting dental plaque comprising contacting dentin with the oral composition of claim 1.

22. A method for inhibiting dental plaque comprising contacting dentin with the oral composition of claim 2.

23. A method for inhibiting dental plaque comprising contacting dentin with the oral composition of claim 18.

24. A method for inhibiting dental plaque comprising contacting dentin with the oral composition of claim 19.

25. A method for inhibiting dental plaque comprising contacting dentin with the oral composition of claim 20.

* * * * *